United States Patent
Czaniera (10) Patent No.: US 8,574,152 B2
(45) Date of Patent: *Nov. 5, 2013

(54) PROCESS AND ARRANGEMENT FOR THE PRODUCTION OF A SIGNAL THAT CORRESPONDS TO THE OPENING STATUS OF THE VOCAL CORDS OF THE LARYNX

(75) Inventor: Juergen Czaniera, Bonndorf (DE)

(73) Assignee: Atmos Medizintechnik GmbH & Co. KG, Lenzkirch (DE)

( * ) Notice: Subject to any disclaimer, the term of this patent is extended or adjusted under 35 U.S.C. 154(b) by 1268 days.

This patent is subject to a terminal disclaimer.

(21) Appl. No.: 11/709,281

(22) Filed: Feb. 22, 2007

(65) Prior Publication Data

US 2007/0208225 A1    Sep. 6, 2007

(30) Foreign Application Priority Data

Feb. 23, 2006 (DE) .......................... 10 2006 008 990

(51) Int. Cl.
| | |
|---|---|
| *A61B 1/00* | (2006.01) |
| *A61B 1/04* | (2006.01) |
| *A61B 1/06* | (2006.01) |
| *A61B 1/267* | (2006.01) |

(52) U.S. Cl.
CPC .............. *A61B 1/267* (2013.01); *A61B 1/2673* (2013.01)
USPC ............ 600/178; 600/160; 600/188; 600/109

(58) Field of Classification Search
CPC ... A61B 1/00158; A61B 1/267; A61B 1/2673
USPC ......... 600/109, 160, 178, 181, 185, 188, 189, 600/199, 473, 476, 478
See application file for complete search history.

(56) References Cited

U.S. PATENT DOCUMENTS

| | | | | |
|---|---|---|---|---|
| 4,273,959 | A * | 6/1981 | Tuda et al. ..................... | 704/276 |
| 4,810,875 | A * | 3/1989 | Wyatt ........................ | 250/227.11 |
| 4,898,175 | A * | 2/1990 | Noguchi ....................... | 600/476 |
| 4,909,261 | A | 3/1990 | Rothenberg | |
| 4,953,539 | A * | 9/1990 | Nakamura et al. ............ | 600/109 |
| 5,246,002 | A * | 9/1993 | Prosser ........................ | 600/336 |

(Continued)

FOREIGN PATENT DOCUMENTS

| | | |
|---|---|---|
| DE | 26 02 307 A1 | 7/1976 |
| DE | 10 2004 011 147 B3 | 11/2005 |

(Continued)

*Primary Examiner* — John P Leubecker
*Assistant Examiner* — Arnaldo Torres Diaz
(74) *Attorney, Agent, or Firm* — Nath, Goldberg & Meyer; Jerald L. Meyer; Stanley N. Protigal (57) ABSTRACT

An arrangement is described in which an endoscope 3 inserted into the pharynx of the patient B is used to visually examine the vibrations of the vocal cords 2, while using light that contains little or no infrared light. At the same time, an oscillogram of the vibrations of the vocal cords is plotted, showing the sequence of motion of the vocal cords. The latter purpose is served by an emitter 1, which is attached to the throat of the patient B below the vocal cords 2 and which produces light in the near infrared range (NIR). Using a mirror 5 that reflects infrared light, the light modulated by the vibration of vocal cords is coupled out and fed to a sensor 6, which, together with an evaluating unit 9, detects and evaluates the vocal cord signals.

12 Claims, 6 Drawing Sheets

(56) References Cited

U.S. PATENT DOCUMENTS

| | | | |
|---|---|---|---|
| 5,517,997 A * | 5/1996 | Fontenot | 600/473 |
| 6,032,070 A * | 2/2000 | Flock et al. | 600/473 |
| 6,161,537 A * | 12/2000 | Gravenstein et al. | 128/200.26 |
| 6,507,747 B1 * | 1/2003 | Gowda et al. | 600/407 |
| 6,530,882 B1 * | 3/2003 | Farkas et al. | 600/168 |
| 6,734,893 B1 * | 5/2004 | Hess et al. | 348/68 |
| 6,796,938 B2 * | 9/2004 | Sendai | 600/109 |
| 2004/0082863 A1 * | 4/2004 | McGreevy et al. | 600/476 |
| 2005/0027166 A1 * | 2/2005 | Matsumoto et al. | 600/162 |
| 2005/0182321 A1 * | 8/2005 | Frangioni | 600/431 |
| 2005/0219376 A1 | 10/2005 | Wittenberg et al. | |
| 2005/0279354 A1 * | 12/2005 | Deutsch et al. | 128/200.24 |
| 2006/0020172 A1 | 1/2006 | Luerssen et al. | |
| 2006/0069314 A1 | 3/2006 | Farr | |
| 2006/0079737 A1 | 4/2006 | Heaton et al. | |
| 2006/0287582 A1 * | 12/2006 | Toda | 600/178 |

FOREIGN PATENT DOCUMENTS

| | | |
|---|---|---|
| DE | 10 2004 035 269 A1 | 2/2006 |
| DE | 10 2006 008 990 A1 | 9/2007 |
| EP | 0 383 703 A2 | 8/1990 |
| EP | 1 859 727 A1 | 11/2007 |
| GB | 1 533 112 | 11/1978 |

* cited by examiner

PROCESS AND ARRANGEMENT FOR THE PRODUCTION OF A SIGNAL THAT CORRESPONDS TO THE OPENING STATUS OF THE VOCAL CORDS OF THE LARYNX

The disclosure relates to a process for producing a signal that corresponds to the opening status of the vocal cords of the larynx, as well as to an arrangement for implementing this process.

The so-called vocal cord signal is proportional to the opening status of the vocal cords and can be depicted or plotted, e.g., as a time-dependent curve.

The human voice and human language come into being through a complex interaction of the breath, the vibrations of the vocal cords, and the shape of the vocal tract. Of comparable complexity are the disease patterns and clinical pictures of the voice. In giving a comprehensive diagnosis it is therefore important to analyze not only the acoustic parameters but also the vibrations of the vocal cords as the source of sound.

Unlike the movements of a pendulum, these vibrations are movements that are difficult to comprehend and describe. Rather, they are complicated, three-dimensional sequences that involve the vocal cords in a gradual process of opening, under the effect of varying air pressure, produced by the lungs, and tension in the vocal cords voluntarily exerted by the speaker or singer. The vocal cords may be subject to many anomalies, e.g., incomplete closure, unilateral paralysis, abnormal opening behavior, and irregular transient effects. The investigation of these anomalies will provide the investigator with information on the disease.

A fact that makes such investigations more difficult to undertake is that the vocal cords can only be observed and analyzed endoscopically or with indirect methods, since that vibrations of the vocal cords lying in the range from 70 Hz to 1,000 Hz cannot be observed in direct optical fashion due the rapid sequence of movement.

At this time the recognized and customary process employed for the indirect investigation of vocal cord vibrations is known as electroglottography. With this process the opening of the vocal cords can be depicted in the form of a time-curve that resembles an oscillogram. Here a weak high-frequency current is conducted through the area of the larynx by means of electrodes positioned on the patient's throat. The current is modulated by the opening and closing movements of the vocal cords, and these movements modify the resistance slightly. This modulated current is measured and is depicted in the form of a curve.

This process makes possible a complete record that is continuous over time for the patterns of vocal cord movement, and thus also makes possible an evaluation of the transient effects. The process also permits a judgment to be made on the very complex process by which the vocal cords open, since resistance increases when the vocal cords are opened from below by pressure on the side facing the lungs, but remain completely closed on the side facing the pharynx. The process thus permits a kind of view into the third dimension of the vibratory events.

Since the electroglottographic process must operate with the very small signals to insure the safety of the patient (who is directly connected to the electrodes), the evaluation of the signals obtained in this manner is a costly one. When it is necessary to optically observe the vocal cords at the same time, separate endoscopic equipment is required.

On the other hand, an optical examination and evaluation of the vocal cords is possible with stroboscopic processes, in which the vocal cords are observed endoscopically or by means of a laryngoscope. Here the light sources, or camera, are controlled in a manner that is synchronized with the vibrations of the vocal cords. Synchronization or, as the case may be, triggering is generally performed using vocal cord vibrations recorded with a microphone or with electronic phase-shifting equipment that is manually adjustable. In these stroboscopic processes the vocal cords, which are in a state of vibration, appear either in slow motion or at rest, depending on the phase difference. A graphic picture of the vocal cords, either moving or at rest, is thereby provided that can be evaluated visually with a high degree of success.

The disadvantage of this method is that it does not provide a view, continuous over time, of the visually perceived vibrations, which are composed of many real vibrations. As a result, a view of the vocal cords is only possible in the steady-state state for periodic vibrations. Transient effects cannot be observed and evaluated.

Also impossible is an evaluation of the three-dimensional vocal cords, and thus, so to speak, a view into the third dimension, since as long as the vocal cords remain closed on the side facing the pharynx it is possible from above to identify the manner in which the vocal cords open on the side facing the lungs.

Thus for a complete investigation of the vocal cords an electroglottographic examination is necessary, in addition to the endscopic examination employing stroboscopic illumination. To be sure, these two methods complement each other in optimal fashion, though their expense is rather high in terms of required apparatus.

In another known process—that of bi-directional stroboscopy—the examination of the throat tissue below the vocal cords involves a second stroboscopic illumination in a different color. With this process the opened vocal cords can be displayed with a high degree of contrast vis-à-vis the surrounding tissue, and this permits a simplified, computer-based digital evaluation of the images.

A disadvantage of bi-directional stroboscopy is that mentioned above: transient effects cannot be depicted.

Finally, high-speed video cameras are employed to examine the vocal cords. In this process the endoscopic image of the vocal cords is measured at an image repetition rate that is high relative to vocal cords'rate of vibration. The video recordings can then be viewed in slow motion, so that a more precise visual judgment of vibrations is possible. This process permits an examination that is continuous over time, since it is not dependent on a steady-state, periodic condition, and transient effects can be examined, unlike in the stroboscopic method. To be sure, the technical expense is not inconsiderable. Furthermore, the quality of the display is poorer due to lower image resolution and reduced brightness. A disadvantage also rests in the fact that the video recording can only be viewed after the fact, in slow motion. When there are inadequacies in the recording which become evident only when the recording is viewed, the recording must be remade.

Finally this process, like the stroboscopic method, only permits an examination of the vocal cords from above. Movements of the vocal cords identifiable on the side facing the lungs cannot be evaluated as long as the vocal cords remain closed on the side facing the pharynx.

Thus, in the prior art the most ideal approach is still a combination of a stroboscopic process and an endoscopic examination of the vocal cords using an electroglottographic process that records the movements of the vocal cords in the form of an oscillogram. Due to the considerable expense in terms of apparatus, however, devices that are suitable for this combination—known on the market by the brand name "Laryngograph"—are rather costly.

The present disclosure describes a less expensive process for the visual examination of the vocal cords and at the same time of providing a display of the vibrations of the vocal cords in the form of an oscillogram.

This problem is solved by producing a signal which corresponds to the opening status of the vocal cords of the larynx, in which process the vocal cords are illuminated with a light source and are optically examined with an endoscope, and a signal, which is modulated by the movement of the vocal cords, is displayed and/or recorded. The vocal cords are illuminated not only with light of a wavelength longer than 600 nm, chiefly with light in the near-infrared range, so-called NIR light, but also with visible light that contains little infrared light, and particularly light that contains no infrared light. The intensity of the NIR light is modulated by the movement of the vocal cords, is received by a sensor, and is detected, in order to generate a vocal cord signal that can be presented in visual form. In order to permit the simultaneous endoscopic examination of the vocal cords, without interfering with the vocal cord signal, light that contains little or no infrared light is used, thus permitting the vocal cord signal be separated from the image signal in a simple fashion.

The use of NIR light provides the decisive advantage, in that this light, whose wavelength lies in the range from 0.8 µm to 1.2 µm, is particularly suited for penetrating human tissue, inasmuch as this light is not highly absorbed by water, nor by the chromophores melanin and hemoglobin.

At the same time, light of this wavelength can be transmitted relatively free of loss by the glass fibers of the optical guides and lenses belonging to the endoscope. Unsuited here are liquid optical guides, which have poor transmission characteristics for light in the wavelength range around 0.9 µm.

Well-suited for generating the NIR light are light-emitting diodes, so-called LEDs, as well as lasers, by means of which light of high intensity, and with good focusing qualities, can be generated. This applies both to light sources for producing visible light containing little or no infrared light and to light sources for producing the NIR light.

The application of conventional endoscopic light sources, e.g., halogen and xenon emitters, is unsuitable here, since their radiation would mask the signal produced by the NIR light source due to the high portion of NIR light.

The process is highly suited for the stroboscopic examination of the vocal cords since, as in the known methods, the stroboscopic light source can be synchronized using the vocal cord signal.

Proposed for the practical realization of the process is an arrangement in which an emitter for generating relatively strong NIR radiation is applied to the patient's throat at a point below the larynx. This radiation illuminates the trachea by passing from the outside through the tissue in the area below the vocal cords. This NIR light, invisible to the human eye, passes through the opening vocal cords and into the patient's pharyngeal cavity. From there it passes through the endoscope introduced into the pharynx and reaches a sensor serving to receive vocal cord signals. Since human tissue is permeable to NIR light to only a limited degree, the NIR light passing through the vocal cords is modulated by the movement of the vocal cords. Due to the transmission properties of human tissue, with this vocal cord signal a signal of lower amplitude is also advantageously generated if the vocal cords remain closed on the side facing the pharynx, but are already open on the side facing the lungs.

In a manner that is comparable to that of electroglottography, the process according to the invention is thus able to provide information on the movement of the vocal cords which is not optically visible with an endoscope.

In terms of apparatus, the configuration for implementing the process according to the invention is particularly simple since, the vocal cord signals aside, the same endoscope serves to provide light with little or no infrared light and to examine the vocal cords.

The NIR light can be conducted through the optical system of the endoscope in a particularly simple manner if the NIR light is coupled out on the side of the configuration that exhibits the illumination source or camera, and is fed to the sensor. This NIR light is coupled out using a mirror or prism which is transparent to light with little or no infrared light but which reflects NIR light.

In this arrangement the same results can be achieved as in electroglottography, but with a considerably reduced technical expense, greater patient safety, and a simpler process.

Since the same endoscope is used in generating the vocal cord signals as in the stroboscopic examination of the vocal cords, and since the source for generating the light with little or no infrared light and the source for NIR light are not mutually disruptive, the two complementary diagnostic procedures can be performed simultaneously, and the measuring results can be recorded and correlated.

Next the process according to the invention, as well as examples of arrangements for implementing the process, will be explained in detail on the basis of drawings. Shown in the drawings are:

FIG. 1 schematic cross-section of the vocal cords in various opening stages, specifically FIG. 1a the vocal cords completely closed FIG. 1b the vocal cords in the process of opening FIG. 1c the vocal cords opened FIG. 2 lower view of the vocal cords shown in FIG. 1, in the same stages shown in FIGS. 1a, b, and c FIG. 3 schematic depiction of the arrangement according to the invention in an initial exemplary embodiment, showing the head of the observer and the head of the patient FIG. 4 enlarged detail of FIG. 3

FIG. 5 arrangement according to the invention in a second exemplary embodiment, showing the patient's head FIG. 6 enlarged detail of FIG. 5

FIG. 7 arrangement according to the invention in a third exemplary embodiment, showing the head of the observer and that of the patient FIG. 8 enlarged detail of FIG. 7

FIG. 9 arrangement according to the invention in a fourth exemplary embodiment, showing the head of the observer and that of the patient FIG. 10 enlarged detail of FIG. 9

FIG. 11 arrangement according to the invention in a fifth exemplary embodiment, showing the head of the observer and that of the patient FIG. 12 enlarged detail of FIG. 11, and FIG. 13 section along line XIII-XIII in FIG. 11.

The process according to the invention serves the examination of the vocal cord movement, particularly in diagnosing the opening and closing movement on the side of the vocal cords that lies opposite the larynx.

Figures 1, 1A, 1B, 1C:
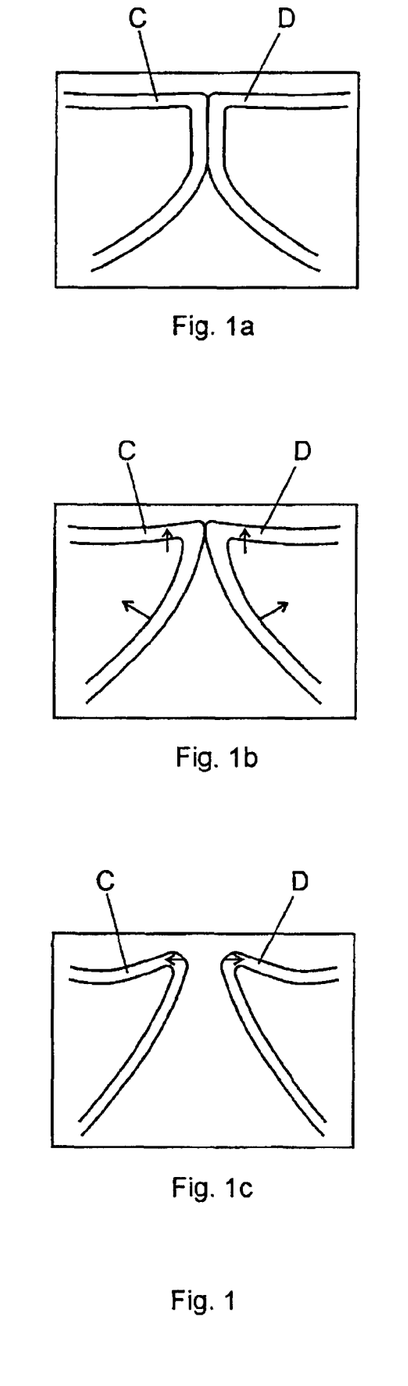
Figures 2, 2A, 2B, 2C:
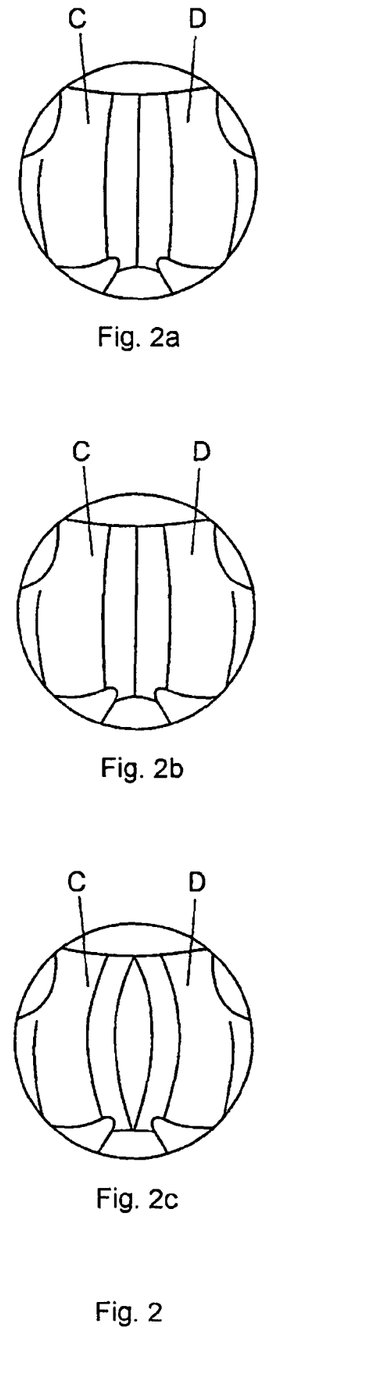

The two vocal cords C and D and their course of movement are illustrated in the schematic depiction provided by FIGS. 1 and 2.

FIGS. 1a and 2a depict the vocal cords C and D as they rest against each other, i.e., the vocal cords in a completely closed state.

Under the influence of air pressure produced by the lungs and through voluntary tension, the vocal cords C and D open in the direction of the arrows shown in FIGS. 1b and 1c, until they reach the fully opened state indicated in FIGS. 1c and 2c.

This course of movement can be diagnosed with the configuration according to the invention.

Figures 3, 4:
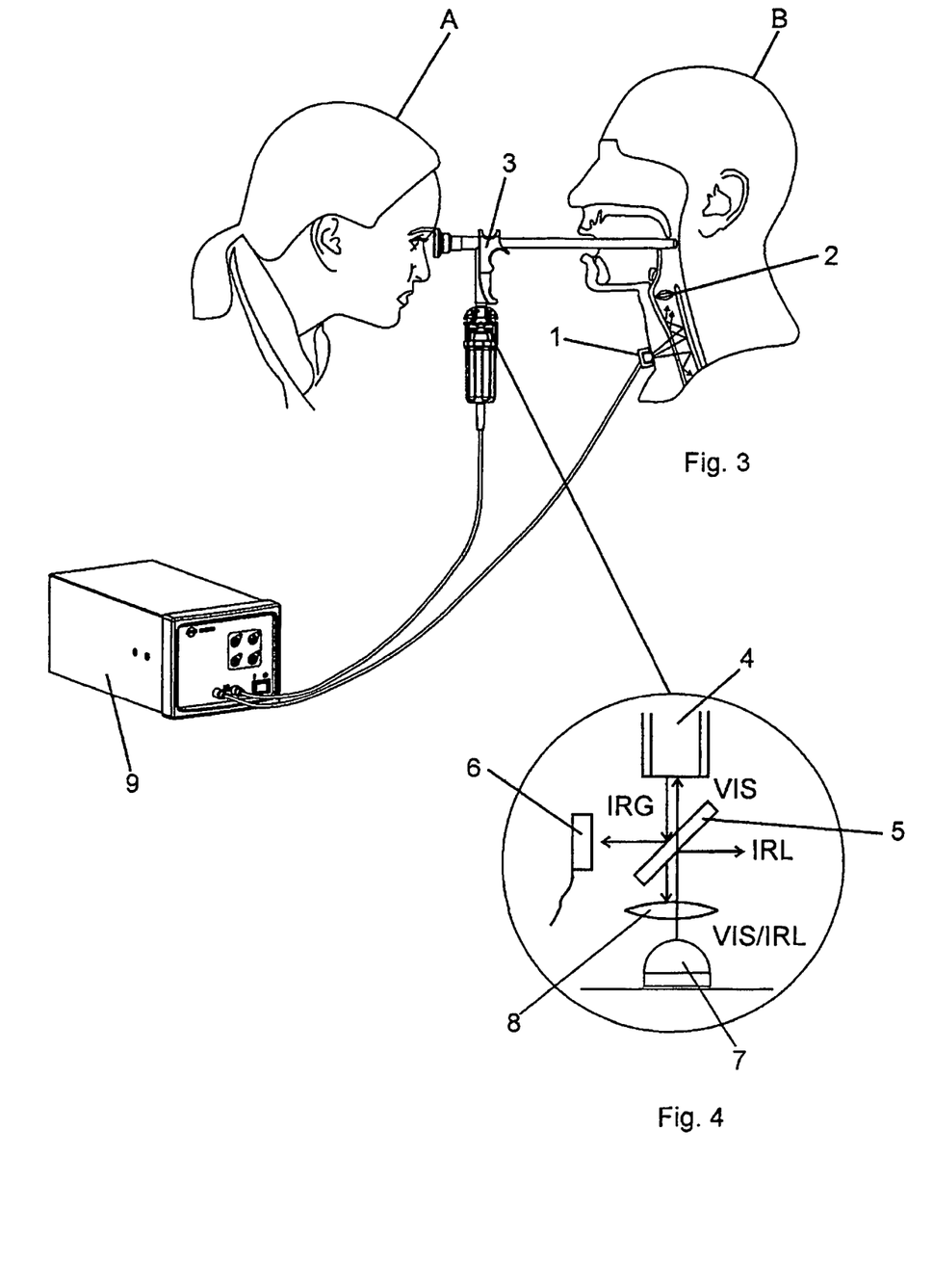

In an initial exemplary embodiment, the configuration basically consists of an endoscope 3, which is inserted into the pharyngeal cavity of the patient B and is used by the examiner—e.g., a physician—to optically examine the vocal cords 2. Light from a light source 7 is fed into the illumination entranceway 4 of the endoscope in conventional fashion. A novelty of the configuration rests in the fact that the light employed is exclusively light containing little or no infrared light. To achieve this end, the light produced by the light source 7, to the extent that it contains portions of infrared light, is conducted to an infrared light mirror 5, which reflects the infrared light—and thus couples it out—and transmits only light in the visible wavelength range.

Positioned below the larynx of the patient B is an emitter 1 that produces light in the near-infrared range, specifically NIR light. The light generated by this emitter 1 penetrates the throat tissue and illuminates the trachea, and thus the vocal cords 2, from below. This light penetrates the vocal cords 2 to a greater or lesser degree, depending on the degree to which they are opened (depicted in FIGS. 1 and 2), and thus reaches the endoscope 3. The light traverses the light guides of the endoscope 3, passes the illumination entranceway 4, and reaches the mirror 5 for infrared light. This mirror takes the infrared light IRG leaving the illumination entranceway 4 of the endoscope and reflects it onto the infrared light sensor 6. Since the intensity of this infrared light IRG is modulated by the movement of the vocal cord aperture (the glottis), the sensor 6 produces a signal that corresponds to the movement of the vocal cords.

The visible light that contains little or no infrared light and that leaves the illumination entranceway 4 passes through the mirror, without being reflected, with the result that the vocal cord signal is not distorted or masked.

The signals detected by the sensor 6 are fed to the evaluating unit 9. If a stroboscopic light source is used for the light source 7, it can be triggered by the vocal cord signals using the evaluating unit 9.

Figures 5, 6:
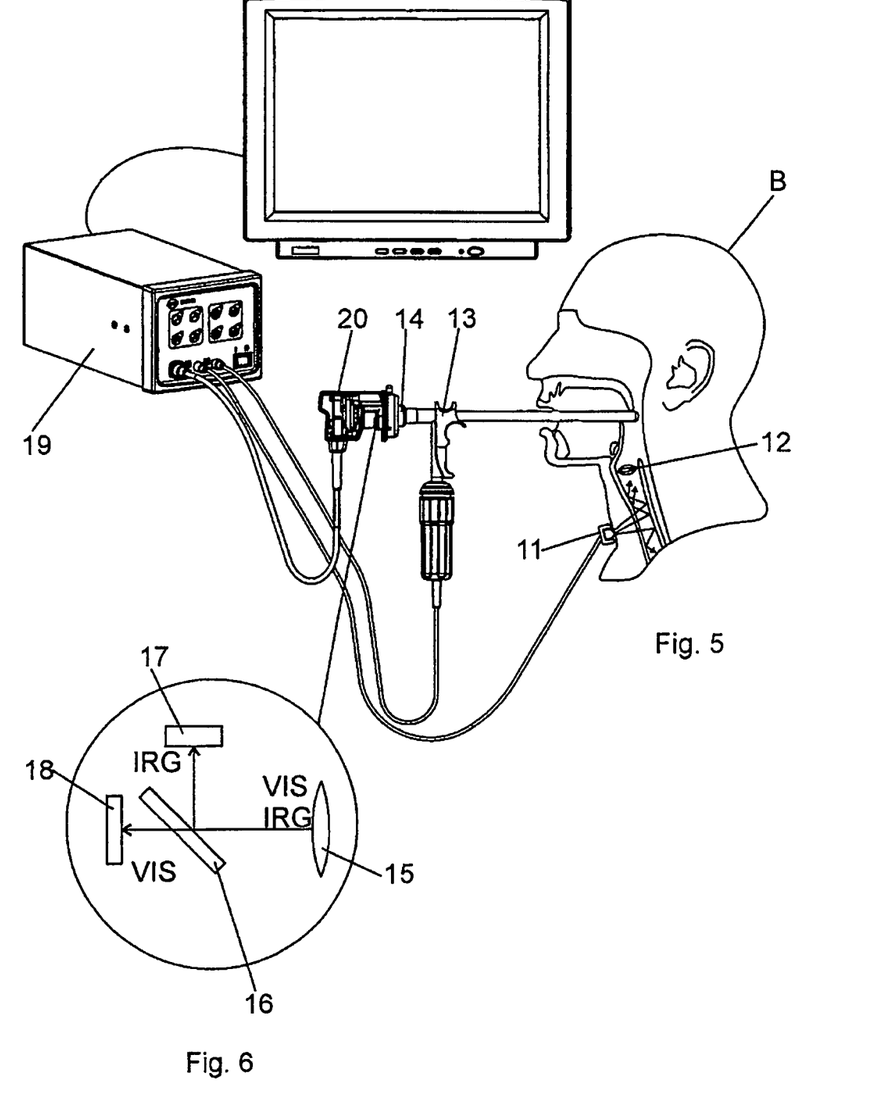

The arrangement according to the invention can be modified when a video camera is used. This is illustrated by FIGS. 5 and 6. In this configuration, too, infrared light is produced by an emitter 11 positioned below the larynx of the patient B. The infrared light penetrates the tissue of the throat and illuminates the trachea, and thus the vocal cords 12, from below. In the same fashion as explained in relation to FIGS. 3 and 4, the infrared light penetrates the vocal cords 12 to a greater or lesser degree, with the result that the vocal cord signal modulated by the movement of the vocal cords is fed to the visual lens system of the endoscope 13. Unlike in the configuration shown in FIGS. 3 and 4, however, this vocal cord signal is fed to a video camera 20 via the eyepiece 14 of the endoscope 13. As illustrated in FIG. 6, an IR mirror 16 is located in the optical path between the camera lens 15 and the image sensor 18 of the video camera. By means of this IR mirror 16, the light signal IRG modulated by the opening of the vocal cords 12—i.e., the vocal cord signal—is coupled out and fed to an infrared sensor 17.

The visible light VIS, on the other hand, penetrates the infrared mirror 16 and produces an image of the vocal cords 12 on the image sensor 18 of the camera 20. The infrared mirror 16 insures that the visible light cannot distort or mask the vocal cord signals.

The image signals produced by the camera 20, as well as the vocal cord signals, are fed to the evaluating unit 19 and displayed on a monitor 10.

Figures 7, 8:
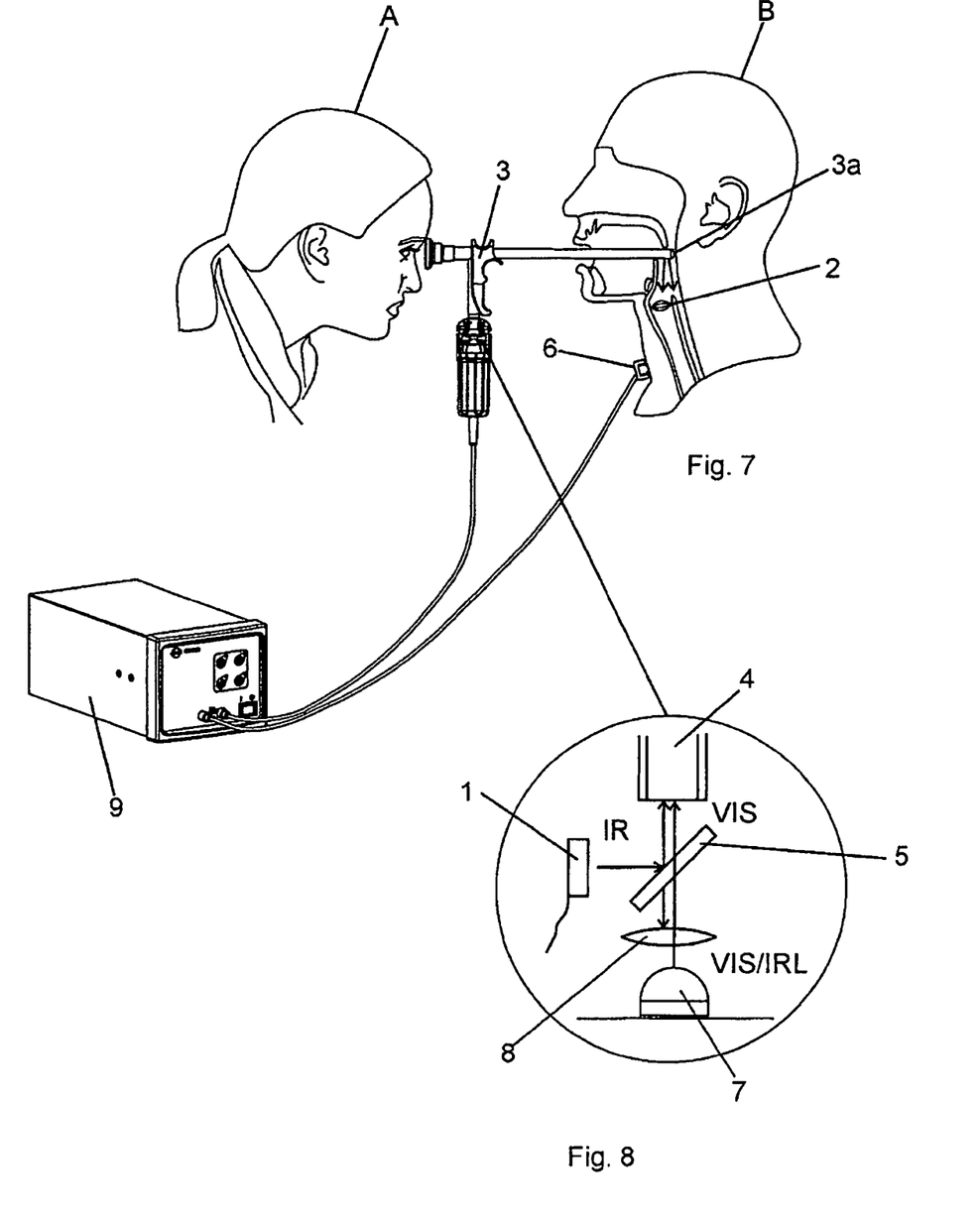

As shown in FIGS. 7 and 8, the process according to the invention can also be implemented with an arrangement in which the infrared sensor and the emitter for NIR light are reversed.

As in the exemplary embodiments explained above, the visible light VIS is produced with a light source 7 and focused by a lens 8. After passing through the infrared mirror 5 it travels through the illumination entranceway 4 and enters the light guides of the endoscope 3. If the light source 7 contains infrared light IRL, this light is coupled out by an infrared mirror 5 in the manner described in relation to FIG. 4.

The same infrared mirror 5 serves to reflect the infrared light produced by the NIR emitter 1. This light travels through the illumination entranceway 4 and enters the light guides of the endoscope 3, leaving at the distal end 3a and moving in the direction of the arrows. It passes through the vocal cords 2 and is modulated by them to produce the vocal cord signal and is then received and detected by a sensor attached to the throat of the patient B at a point below the larynx. This signal is fed to the evaluating unit 9.

In a simplified form, this arrangement may entirely omit the NIR emitter 1 and the infrared mirror 5, if the light produced by the light source 7 contains light in the NIR range in sufficient measure.

Figures 9, 10:
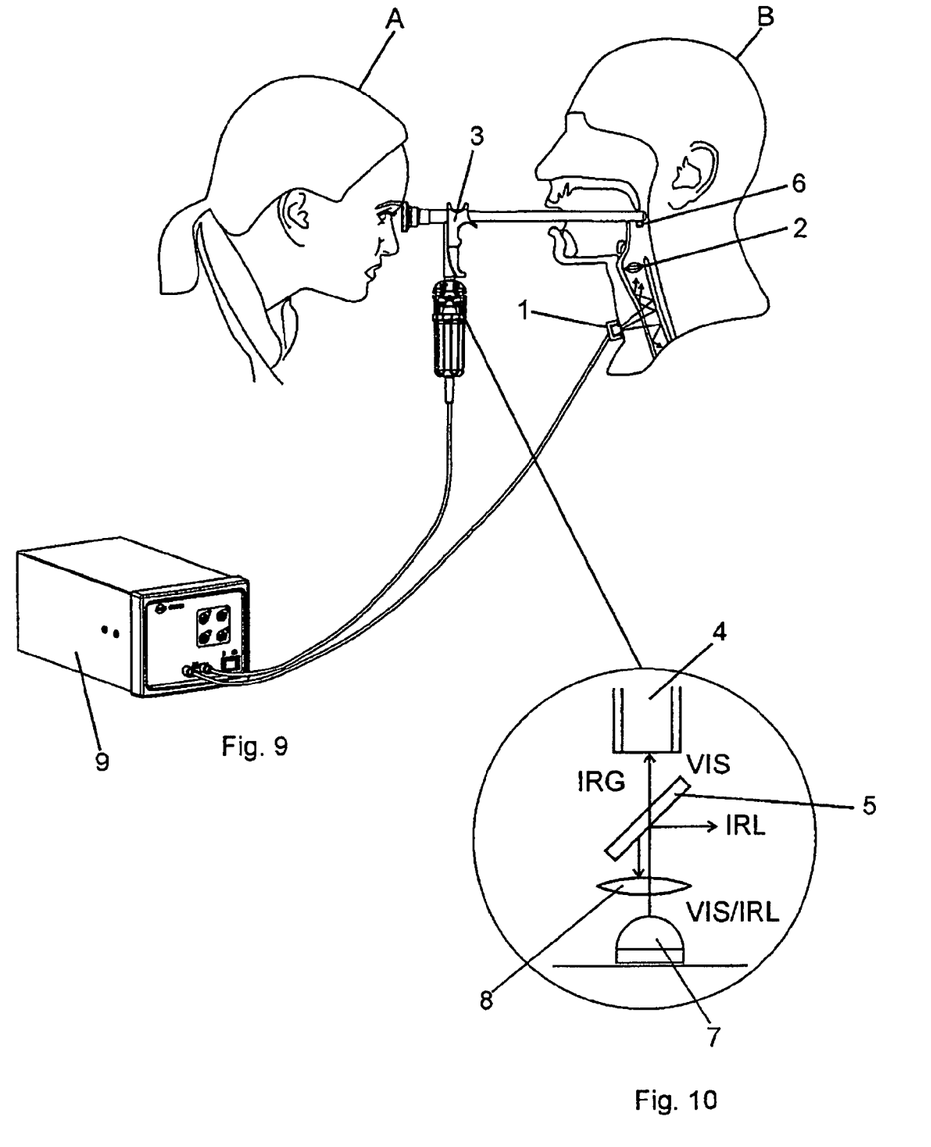

In another proposed version of the invention, shown in FIGS. 9 and 10, the light signal modulated by the vocal cords is not coupled out from the illumination entranceway 4, but is received by an NIR sensor 6 attached at the distal end 3a of the endoscope.

If the employed light source 7 contains infrared light IRL as well as visible light VIS, this infrared light IRL must again be coupled out, so that the light used to illuminate the vocal cords 12 does not mask and distort the vocal cord signal.

Figures 11, 12, 13:
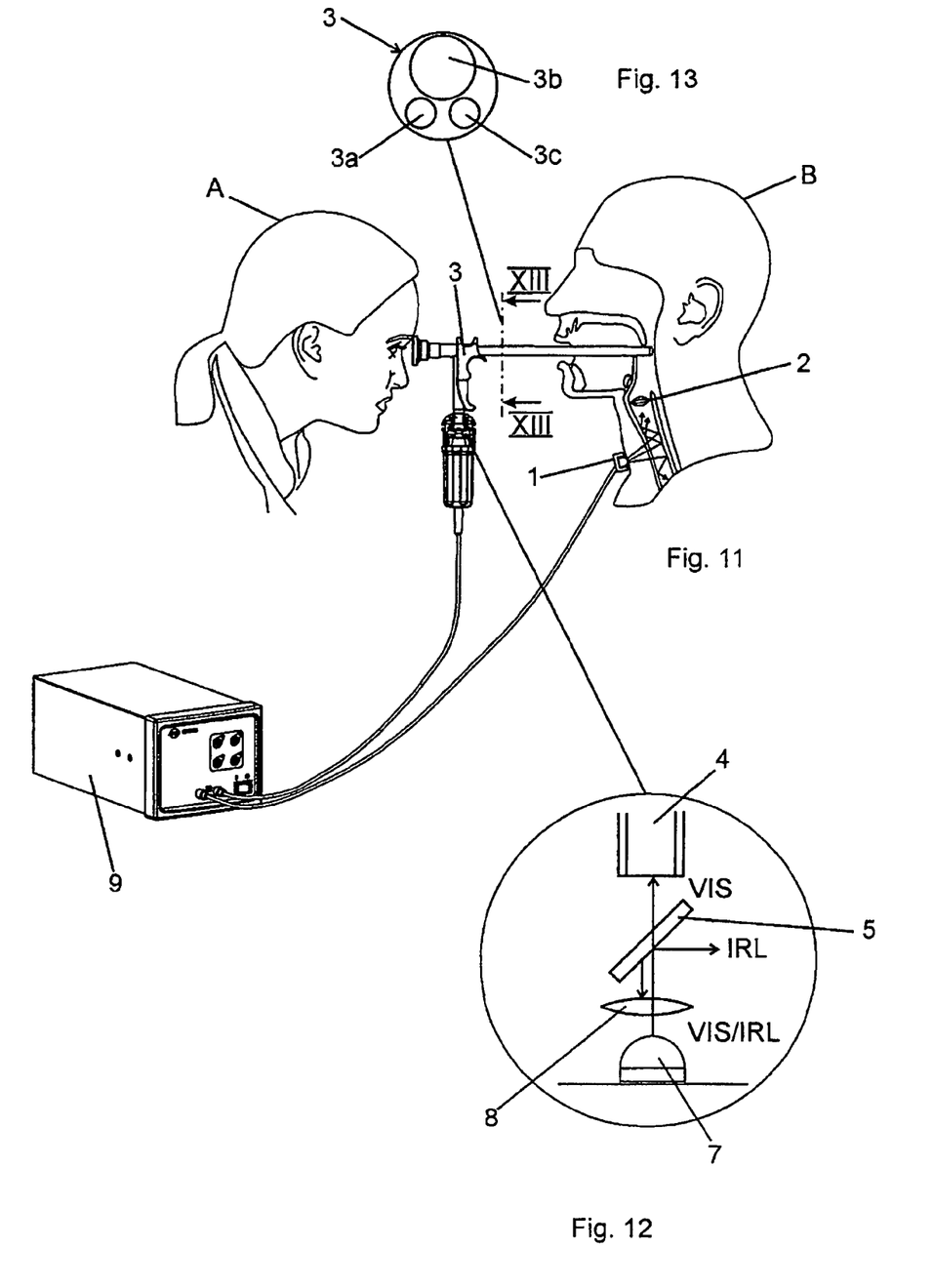

A better signal separation can be achieved with the configuration illustrated in FIGS. 11 and 12. This configuration employs an endoscope whose shaft contains a separate image channel 3a for the endoscope lens, as well as an illumination channel 3c for guiding the VIS light produced by the light source 7, and a sensor channel 3d for the further passage of the vocal cord signals. Only light containing little or no infrared light need be fed into the illumination entranceway 4. If the light source 7 produces infrared light IRL in addition to light in the visible range VIS, this infrared light IRL can be coupled out with an infrared light mirror 5, in the manner described above.

List of Reference Symbols
1 emitter for NIR light
2 vocal cords
3 endoscope
3a distal end
3b image channel
3c illumination channel
3d sensor channel
4 illumination entranceway
5 IR mirror
6 sensor for NIR light
7 light source
8 lens
9 evaluating unit
10 display screen
11 emitter for NIR light
12 vocal cords
13 endoscope
14 eyepiece of endoscope
15 lens of video camera, camera lens
16 IR mirror
17 sensor 18 image sensor of video camera
19 evaluating unit
20 video camera
A server
B patient
ING IR light modulated by the vocal cords (vocal cord signal)
VIS visible light
IRL infrared light

The invention claimed is:

1. A method for producing a signal which corresponds to a movement of the vocal cords of the larynx, comprising:
   simultaneously illuminating the vocal cords with visible light providing stroboscopic examination of the vocal cords and with continuous light having a wavelength longer than 600 nm in a manner which allows modulation of the continuous light without interference from the visible light and without the visible light interfering with the modulation of the continuous light;
   optically examining the movement of the vocal cords with an endoscope using the visible light;
   detecting a light beam having a wavelength longer than 600 nm modulated by the movement of the vocal cords;
   generating a vocal cord signal from the detected modulated light beam; and
   performing at least one of displaying and recording the vocal cord signal.

2. The method according to claim 1, further comprising:
   using the vocal cord signal as a synchronization signal; and
   illuminating the vocal cords with visible light from a stroboscopic light source triggered by the synchronization signal.

3. An apparatus for producing a signal which corresponds to a movement of the vocal cords of the larynx, comprising:
   an emitter attachable to a throat of a patient and configured to illuminate the vocal cords with light having a wavelength longer than 600 nm;
   an endoscope configured for insertion into a pharynx of the patient;
   an endoscopic light source configured to stroboscopically illuminate the vocal chords with visible light simultaneously with the emitter in a manner which allows modulation of the light having a wavelength of longer than 600 nm without interference from the visible light and without the visible light interfering with the modulation of the continuous light; and
   a sensor configured to detect a vocal chord signal in the form of light having a wavelength longer than 600 nm modulated by the movement of the vocal chords.

4. The apparatus according to claim 3, further comprising:
   an endoscopic optical system configured to receive the visible light; and
   a mirror or prism configured:
   to reflect to the sensor the light having a wavelength longer than 600 nm modulated by the vocal chords; and
   to transmit the visible light to the endoscopic optical system.

5. The apparatus according to claim 4, wherein the mirror or prism is positioned between the light source and an illumination entranceway of the optical system endoscope and configured such that:
   infrared light coming from the endoscopic light source is reflected away from the sensor; and
   the vocal cord signal is reflected to the sensor.

6. The apparatus according to claim 4, further comprising:
   a camera lens connected to the endoscope; and
   a second mirror or prism positioned behind the camera lens and configured to reflect the vocal cord signal to the sensor and transmit the visible light to a camera.

7. The apparatus according to claim 3, wherein the sensor is positioned at a distal end of the endoscope.

8. The apparatus according to claim 3, further comprising:
   an endoscope illumination channel configured to transmit visible light;
   an image channel configured to transmit an image of the vocal cords to an eyepiece of the endoscope or to a video camera; and
   a sensor channel configured to transmit the vocal cord signal to the sensor.

9. An apparatus for producing a signal which corresponds to a movement of the vocal cords of the larynx, comprising:
   an endoscope configured for insertion into a pharynx of a patient;
   an emitter attached to the endoscope and configured to simultaneously stroboscopically illuminate the vocal cords with visible light and with light having a wavelength longer than 600 nm in a manner which allows modulation of the continuous light without interference from the visible light and without the visible light interfering with the modulation of the continuous light; and
   a sensor attachable to a throat of a patient and configured to detect a vocal chord signal in the form of light having a wavelength longer than 600 nm modulated by the movement of the vocal chords.

10. A method for producing a signal which corresponds to a movement of the vocal cords of the larynx, comprising:
    simultaneously illuminating the vocal cords with visible light providing stroboscopic examination of the vocal cords and with continuous light having a wavelength longer than 600 nm a manner which allows modulation of the continuous light without interference from the visible light and without the visible light interfering with the modulation of the continuous light;
    optically examining the vocal cords using the visible light;
    detecting light having a wavelength longer than 600 nm modulated by movement of the vocal cords;
    generating a vocal cord signal from the detected modulated light;
    performing at least one of displaying and recording the vocal cord signal; and
    providing a camera image of the vocal cords.

11. The method according to claim 10, further comprising:
    using the vocal cord signal as a synchronization signal; and
    illuminating the vocal cords with visible light from a stroboscopic light source triggered by the synchronization signal.

12. The method according to claim 11, further comprising:
    synchronizing the camera image of the vocal chords with the synchronization signal.

* * * * *